（12）United States Patent
Young et al.

(10) Patent No.: US 8,643,835 B2
(45) Date of Patent: Feb. 4, 2014

(54) ACTIVE PLANAR AUTOFOCUS

(75) Inventors: Scott A. Young, Soquel, CA (US);
Daniel L. Cavan, Woodside, CA (US);
Yale Zhang, Sunnyvale, CA (US); Aviv Balan, Mountain View, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 538 days.

(21) Appl. No.: 12/833,093

(22) Filed: Jul. 9, 2010

(65) Prior Publication Data

US 2012/0008137 A1 Jan. 12, 2012

(51) Int. Cl.
*G01N 21/00* (2006.01)
*G01B 11/14* (2006.01)
*G06K 9/00* (2006.01)

(52) U.S. Cl.
USPC .................. 356/237.5; 356/237.1; 356/237.2; 356/237.3; 356/237.4; 356/614; 356/615; 356/620; 356/624; 356/625; 382/145; 382/148; 382/189

(58) Field of Classification Search
USPC ........... 356/237.1–237.5, 614–623, 399–401; 382/145, 148, 149
See application file for complete search history.

(56) References Cited

U.S. PATENT DOCUMENTS

| 4,639,587 | A |  | 1/1987 | Chadwick et al. |
|---|---|---|---|---|
| 4,788,431 | A | * | 11/1988 | Eckes et al. .................. 250/397 |
| 4,971,444 | A | * | 11/1990 | Kato .............................. 356/401 |
| 6,117,598 | A | * | 9/2000 | Imai ................................. 430/22 |
| 6,304,316 | B1 | * | 10/2001 | Jain et al. ........................ 355/53 |
| 6,407,373 | B1 | * | 6/2002 | Dotan ........................ 250/201.3 |
| 7,012,672 | B2 |  | 3/2006 | Van Rhee et al. |
| 7,142,315 | B1 |  | 11/2006 | Lange et al. |
| 2011/0013188 | A1 | * | 1/2011 | Slotboom et al. ............. 356/401 |

* cited by examiner

*Primary Examiner* — Tarifur Chowdhury
*Assistant Examiner* — Sunghee Y Gray
(74) *Attorney, Agent, or Firm* — Luedeka Neely Group, P.C.; Rick Barnes

(57) ABSTRACT

A system for inspecting a depth relative to a layer using a sensor with a fixed focal plane. A focus sensor senses the surface of the substrate and outputs focus data. In setup mode the controller scans a first portion of the substrate, receives the focus data and XY data, and stores correlated XYZ data for the substrate. In inspection mode the controller scans a second portion of the substrate, receives the focus data and XY data, and subtracts the stored Z data from the focus data to produce virtual data. The controller feeds the virtual data plus an offset to the motor for moving the substrate up and down during the inspection, thereby holding the focal plane at a desired Z distance.

6 Claims, 2 Drawing Sheets

ACTIVE PLANAR AUTOFOCUS

FIELD

This invention relates to the field of integrated circuit fabrication. More particularly, this invention relates to auto focus mechanisms, such as are used during the optical inspection of integrated circuits.

INTRODUCTION

The optical inspection of integrated circuits requires very precise control of the desired focal plane. As the term is used herein, "integrated circuit" includes devices such as those formed on monolithic semiconducting substrates, such as those formed of group IV materials like silicon or germanium, or group III-V compounds like gallium arsenide, or mixtures of such materials. The term includes all types of devices formed, such as memory and logic, and all designs of such devices, such as MOS and bipolar. The term also comprehends applications such as flat panel displays, solar cells, light emitting diode arrays, and other substrates containing multiple repeating three dimensional electrical circuitry structures.

Modern integrated circuits often exhibit a sculpted topography. As various layers are deposited and partially removed and new layers are added on top, a surface topography of mesas and valleys (so to speak) develops across the surface of the integrated circuit. Thus, a given process layer of the integrated circuit may or may not exist at any particular X/Y point on the surface of the device. A plane that defines the Z location of this layer might then cut through the mesas and over the valleys.

Unfortunately, the auto focus systems of current inspection tools tend to get confused by one or more of a variety of different factors that are present during integrated circuit inspection. For example, the range of heights and depths in the Z axis of the sculpted surface topography as described above tends to confuse an auto focus mechanism, causing the focal plane to shift from the desired layer (that exists on a single plane) to the ever-shifting level of the surface topography of the integrated circuit (or elsewhere). In addition, noise that is introduced by the movement of the motor and the chuck that moves the substrate relative to the inspection optics can cause the auto focus mechanism to move away from the desired inspection plane. Further, bow across the substrate and vibration that is external to the tool introduce more variables that tend to shift the focal plane away from the desired inspection plane.

What is needed, therefore, is a system that reduces the substrate topography response while generally retaining the ability to respond in real time to other Z disturbances such as substrate bow and vibration.

SUMMARY OF THE CLAIMS

The above and other needs are met by an optical inspection system for inspecting a substrate at a constant layer depth relative to a particular device layer. The inspection system has an image sensor with a fixed focal plane. A focus sensor senses Z distance in regard to the surface topography of the substrate and outputs the Z distance in a focus data stream. The focus sensor and the image sensor are disposed in a known relationship. An XY stage moves the substrate in an XY plane relative to the image sensor and the focus sensor, and a Z motor moves the substrate in a Z dimension relative to the image sensor and the focus sensor. A controller selectively operates the optical inspection system in one of a setup mode and an inspection mode.

In the setup mode the controller controls XY movement of the substrate using the XY stage so as to scan a first portion of the substrate under the focus sensor. The controller receives the focus data stream from the focus sensor, concurrently receives XY data from the XY stage, and stores correlated XYZ data for the first portion of the substrate in a memory. In the inspection mode the controller controls XY movement of the substrate using the XY stage so as to scan a second portion of the substrate under the focus sensor and the image sensor. The controller receives the focus data stream from the focus sensor, concurrently receives XY data from the XY stage, and subtracts the Z distance in the memory from the focus data stream of the focus sensor to produce a virtual data stream, where the Z distance from the memory is correlated with the XY data from the stage. The controller feeds the virtual data stream plus an offset to the Z motor for moving the substrate up and down during the inspection, thereby holding the focal plane at a desired Z distance, regardless of the surface topography of the substrate.

In this manner, the fixed focal plane of the image sensor is held at a desired layer of the integrated circuit, regardless of the differences in the surface topography of the integrated circuit at any given position. Further, the setup mode can be accomplished for a given repeating pattern of the integrated circuits on the substrate, such as for a single die or reticle field. The inspection mode can then be applied to all of the die or reticle fields on the substrate (and for similar substrates) without repeating the setup procedure.

In various embodiments, the first portion is the entire substrate. In other embodiments the first portion is one or more reticle fields of the substrate. In some embodiments the second portion is the entire substrate. In other embodiments the second portion is one or more reticle field of the substrate. In some embodiments the first portion is a subset of the second portion. In other embodiments the first portion is identical to the second portion. In some embodiments the offset is a value that holds the focal plane above the virtual data stream. In other embodiments the offset is a value that holds the focal plane below the virtual data stream.

According to another aspect of the invention there is described a method for inspecting a substrate at constant layer depth relative to a particular device layer of the substrate by controlling XY movement of the substrate so as to scan a first portion of the substrate under a focus sensor, sensing XY position of the substrate during the XY movement, concurrently sensing Z distance in regard to the surface topography of the substrate with the focus sensor, storing correlated XYZ data for the first portion of the substrate, controlling XY movement of the substrate so as to scan a second portion of the substrate under the focus sensor and an image sensor, where the focus sensor and the image sensor are disposed in a known relationship, sensing XY position of the substrate during the XY movement, concurrently sensing Z distance in regard to the surface topography of the substrate with the focus sensor, subtracting the stored Z distance from the sensed Z distance to produce a virtual data stream, where the stored Z distance and the sensed Z distance are correlated by the XY position, moving the substrate up and down relative to the image sensor as directed by the virtual data stream plus an offset, while scanning the second portion of the substrate, thereby holding a focal plane of the image sensor at a desired Z distance, regardless of the surface topography of the substrate, and inspecting the second portion of the substrate at the desired Z distance with the image sensor.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1A:
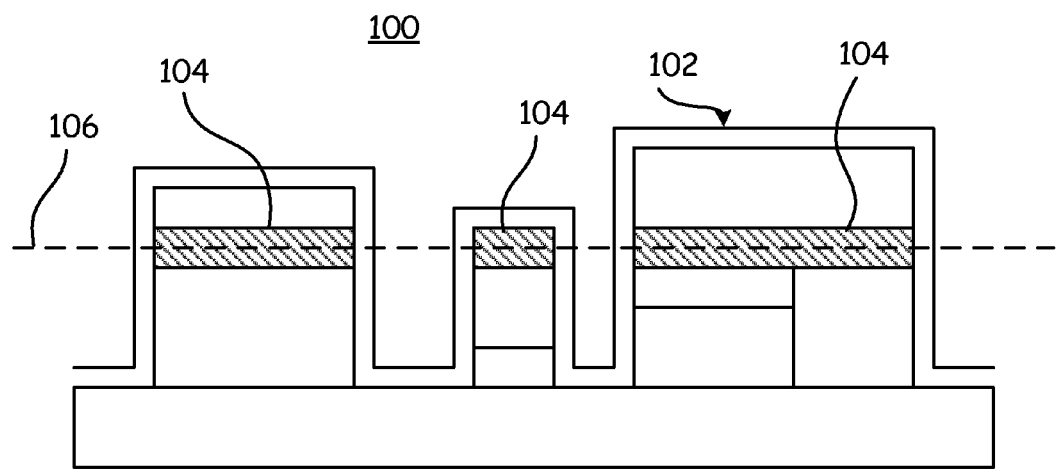
FIG. 1A is a cross sectional diagram of an integrated circuit at a particular process step, showing surface topography and a coplanar inspection layer and focal plane.

With reference now to FIG. 1A, there is depicted a cross sectional diagram of a portion of an integrated circuit 100, showing surface topography 102 and a desired inspection layer 104. It is appreciated that the depiction of FIG. 1 is not intended to represent any specific (or real) integrated circuit 100, but rather just to exemplify different layers having different thicknesses, residing at different depths under the surface, with mesas and valleys etched between portions of a given layer.

Optical inspection tools according to the various embodiments of the present invention hold the focal plane 106 coplanar with the desired inspection layer 104 at all times, regardless of any factors that might be present during the inspection process. For example, factors such as the topography 102 of the integrated circuit 100, floor vibration, chuck bumps, and substrate bow do not cause the focal plane 106 to move away from the desired layer 104. Thus, a focused image of the desired layer 104 is maintained at all times, regardless of such factors.

Figure 1B:
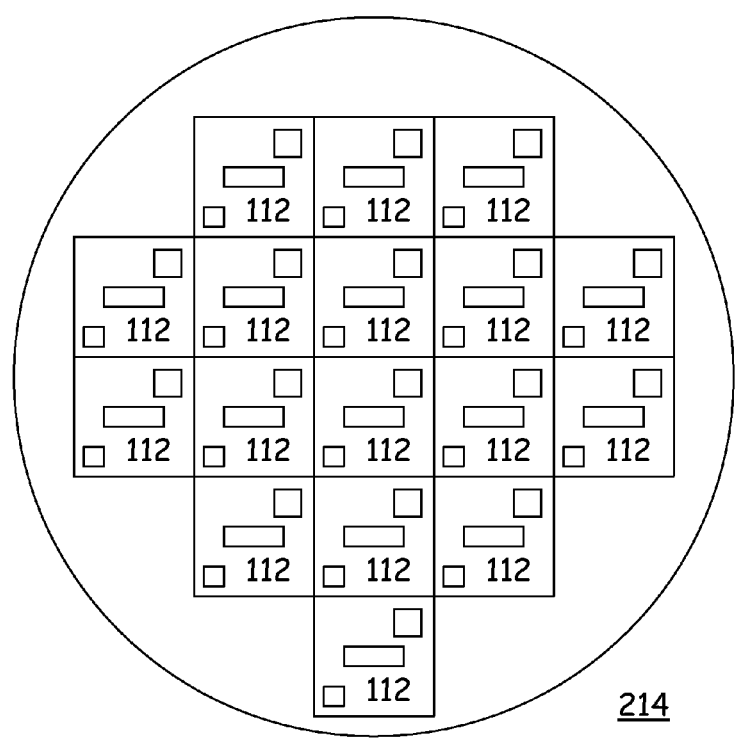
FIG. 1B is a top plan view of a substrate with a repeating matrix of patterns (reticle fields).

With reference now to FIG. 1B there is depicted a substrate 214 with a repeating matrix of patterns (reticle fields) 112 on the substrate 214. These reticle fields 112 represent, for example, individual die on the substrate 214, where the circuit patterns, such as circuit 100 as depicted in FIG. 1A, repeat from one die to the next. These repeating patterns 112 have a constant XY offset from one die pattern to the corresponding portion of the next die pattern. It is appreciated that the example of FIG. 1B is extremely simplified so as to not unnecessarily encumber the drawing with insignificant details.

Figure 2:
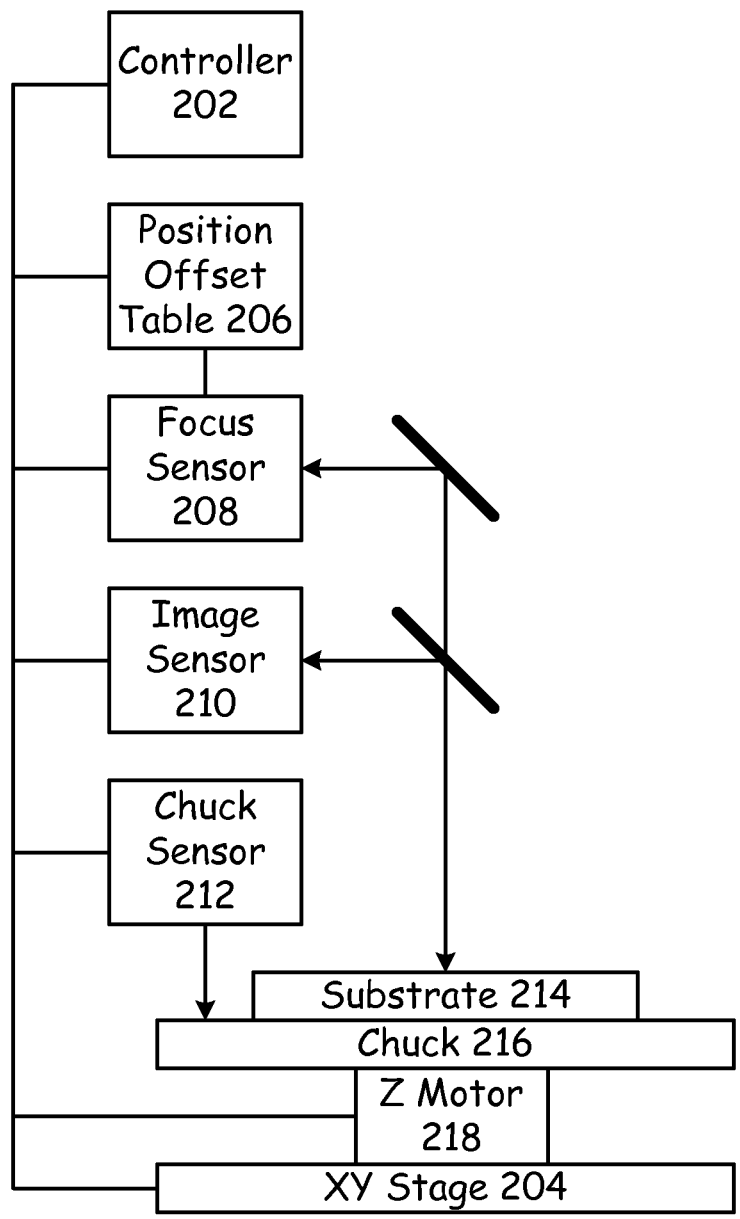
FIG. 2 is a functional block diagram of an apparatus for measuring the topography information of an integrated circuit and for optically inspecting an integrated circuit while maintaining a focal plane to be coplanar with a desired layer of the integrated circuit according to an embodiment of the present invention.

With reference now to FIG. 2, there is depicted a functional block diagram of a processor-based inspection tool 200 for inspecting a layer 104 of an integrated circuit 100 on a substrate 214 according to an embodiment of the present invention. In a standard mode of operation, the tool 200 scans the substrate 214 relative to an image sensor 210. A focus sensor 208 determines the height of the top surface 102 within the particular field of view. The controller 202 takes the height information and uses it to move the z motor 218 so that the top surface 102 the substrate 214 at that particular location is moved toward the focal plane 106.

However, this standard mode of operation continually shifts the focal plane 106 to keep the output of the focus sensor 208 constant. Since the focus sensor 208 is typically sampling a large area of the substrate 214, the actual layer inspected depends upon the topographic content of the particular autofocus field of view being sampled at any given point in time. Further, the response of the focus sensor 208 may be sensitive to the electrical or optical properties of the various layers within the autofocus field of view, thereby further confusing the response of the system 200 and making the actual plane of inspection difficult to determine.

Because of the repeating nature of the reticle fields 112, equivalent XY reticle field positions can be inspected at the same Z position relative to some reference surface. However, if it is desired to keep a specific layer 104 in focus, where the layer 104 does not reside at all locations on the substrate 214 at a set depth relative to the upper surface as described in regard to FIG. 1, then such a simplistic focusing mechanism is insufficient.

Thus, in an advanced mode of operation, the tool 200 senses the topography information 102 from the substrate 214 during a setup process, and compensates for the topography information 102 based on XY location in a feed-forward manner during an inspection process. This process produces what can be thought of as a virtualized surface for the substrate 214. In this manner, setting the focal plane 106 to a given offset from the virtualized surface keeps the focal plane 106 at the desired layer 104, as depicted in FIG. 1.

Thus, the tool 200 compensates for the topography of the substrate 214 using a feed-forward method. However, the tool 200 can still dynamically compensate for variable influences such as Z vibration and the bow of the substrate 214 in a feed-back manner.

Setup Process

The substrate 214 is mounted to a chuck 216 which is mounted to a Z motor 218 which is mounted to an XY stage 204. The XY stage 204 scans the substrate 214 in the XY plane at a fixed height as measured by the chuck sensor 212, so that the focus sensor 208 can detect the surface topography 102 of the substrate 214 at given discrete XY locations of the substrate 214, thereby developing an XYZ map of the topography 102 of the substrate 214. Alternately, only a portion of the substrate 214 is scanned, such as a single reticle field 112.

This map of the topography 102 of the substrate 214 (or reticle field 112) is then further processed to identify topography that is common to all identical reticle field 112 locations across the substrate 214. Topographic features that are not common to all identical reticle field locations 112 across the substrate 214 are mathematically removed from the map data and an averaged reticle field topography map is constructed and stored in a reticle field position offset table 206, which can be located either in the tool 200 or in some accessibly location external to the tool 200.

In some embodiments, the topography map is measured and stored only once for a given substrate containing an integrated circuit 100 at a particular process step, and then is used thereafter during the inspection of all equivalent types of substrates of integrated circuits 100 at the same process step. In other embodiments, mathematical models of the integrated circuit 100 are used to create the topography map, such as might be developed from the design files for the integrated circuit 100. In other embodiments, the topography map is acquired by keeping the autofocus sensor output constant during the XY mapping process and reading the chuck sensor position at each discrete XY location.

Thus, a map of the reticle field 112 topography is constructed, but not of the substrate 214 topography.

Inspection Process

The substrate 214 topography includes both the reticle field 112 topography and other things like the bow of the substrate 214 and the bow of the chuck 216, bumps on the chuck 216, and so forth. Only the reticle field 112 map is played back (subtracted from the focus sensor 208 output signal) during the inspection process. The key to the playback is that the current XY stage 204 position is used as the memory address for the memory bank containing the reticle field 112 topography map. In some embodiments there is no dynamic focusing element for the imaging optics 210. The only thing that is moved to control the image focus is the stage Z, using the Z motor 218. This keeps the optics for the image sensor 210 focused at a given level, regardless of the surface topography. In other embodiments the moving element is not the Z stage with the Z motor 218, but rather a focusing element in the optical path.

In some embodiments, the topography map that is stored in the position offset table 206 is played back during the inspection process in the opposite polarity, so as to cancel the integrated circuit topography response of the auto focus sensor 208. This topography cancellation signal is based on the XY location of the field of view of the image sensor 210. Using this feed-forward method, the integrated circuit 100 topography 102 is no longer tracked up and down by the image sensor 210 optics, and the ideal "planar" response 106 is obtained while still maintaining the ability of the system 200 to track out chuck contamination Z disturbances.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An optical inspection system for inspecting equivalent substrates at constant layer depth relative to a particular device layer of the substrates, the inspection system comprising:
    an image sensor having a fixed focal plane,
    a focus sensor for sensing Z distance in regard to a surface topography of the substrates and outputting the Z distance in a focus data stream, the focus sensor and the image sensor disposed in a known relationship,
    an XY stage for moving the substrates in an XY plane relative to the image sensor and the focus sensor,
    a Z motor for moving the substrates in a Z dimension relative to the image sensor and the focus sensor, and
    a controller for selectively operating the optical inspection system in one of a setup mode and an inspection mode, in the setup mode the controller for,
        controlling XY movement of a first one of the substrates using the XY stage so as to scan only a first reticle field of the first substrate under the focus sensor,
        receiving the focus data stream from the focus sensor,
        concurrently receiving XY data from the XY stage relative to the first reticle field, and
        storing correlated XYZ data for the first portion of the first substrate in a memory,
    in the inspection mode the controller for,
        controlling XY movement of the substrate using the XY stage so as to scan at least one of any other reticle field of the first substrate and any reticle field of any of the other equivalent substrates under the focus sensor and the image sensor,
        receiving the focus data stream from the focus sensor,
        concurrently receiving XY data from the XY stage relative to the scanned reticle field,
        subtracting the Z distance in the memory from the focus data stream of the focus sensor to produce a virtual data stream, where the Z distance from the memory is correlated with the XY data from the stage, and
        feeding the virtual data stream plus an offset to the Z motor for moving the scanned substrate up and down during the inspection, thereby holding the focal plane at a desired Z distance, regardless of the surface topography of the scanned substrate.

2. The optical inspection system of claim 1, wherein the offset is a value that holds the focal plane above the virtual data stream.

3. The optical inspection system of claim 1, wherein the offset is a value that holds the focal plane below the virtual data stream.

4. A method for inspecting equivalent substrates at constant layer depth relative to a particular device layer of the substrates, the method comprising the steps of:
    controlling XY movement of a first one of the substrates so as to scan only a first reticle field of the first substrate under a focus sensor,
    sensing XY position of the first substrate relative to the first reticle field during the XY movement,
    concurrently sensing Z distance in regard to a surface topography of the first substrate with the focus sensor,
    storing correlated XYZ data for the first reticle field of the first substrate,
    controlling XY movement of at least one of any other reticle field of the first substrate and any reticle field of any of the other equivalent substrates, referred to hereafter as a scanned reticle field of a scanned substrate, so as to scan a second portion of the scanned substrate under the focus sensor and an image sensor, where the focus sensor and the image sensor are disposed in a known relationship,
    sensing XY position of the scanned substrate relative to the scanned reticle field during the XY movement,
    concurrently sensing Z distance in regard to the surface topography of the scanned substrate with the focus sensor,
    subtracting the stored Z distance from the sensed Z distance to produce a virtual data stream, where the stored Z distance and the sensed Z distance are correlated by the XY position,
    moving the scanned substrate up and down relative to the image sensor as directed by the virtual data stream plus an offset, while scanning the second portion of the scanned substrate, thereby holding a focal plane of the image sensor at a desired Z distance, regardless of the surface topography of the scanned substrate, and
    inspecting the second portion of the scanned substrate at the desired Z distance with the image sensor.

5. The method of claim 4, wherein the offset is a value that holds the focal plane above the virtual data stream.

6. The method of claim 4, wherein the offset is a value that holds the focal plane below the virtual data stream.

* * * * *